United States Patent
Eder et al.

(10) Patent No.: US 8,869,327 B2
(45) Date of Patent: Oct. 28, 2014

(54) PATIENT SUPPORT APPARATUS AND MEDICAL IMAGING APPARATUS HAVING THE PATIENT SUPPORT APPARATUS

(71) Applicants: Hanns Eder, Bubenreuth (DE); Patrick Gross, Langensendelbach (DE); Martin Requardt, Nürnberg (DE); Martin Ringholz, Erlangen (DE); Markus Schmidt, Nuremberg (DE)

(72) Inventors: Hanns Eder, Bubenreuth (DE); Patrick Gross, Langensendelbach (DE); Martin Requardt, Nürnberg (DE); Martin Ringholz, Erlangen (DE); Markus Schmidt, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/775,497

(22) Filed: Feb. 25, 2013

(65) Prior Publication Data

US 2013/0219620 A1  Aug. 29, 2013

(30) Foreign Application Priority Data

Feb. 29, 2012  (DE) .......................... 10 2012 203 119

(51) Int. Cl.
*A61B 6/04* (2006.01)
*A61G 13/12* (2006.01)
*A61G 7/00* (2006.01)

(52) U.S. Cl.
CPC ............... *A61B 6/0407* (2013.01); *A61G 7/00* (2013.01)
USPC ............. 5/601; 5/600; 5/621; 5/622; 378/209

(58) Field of Classification Search
USPC ....... 5/600, 601, 606, 86.1, 81.1 R, 621–624; 378/209
See application file for complete search history.

(56) References Cited

U.S. PATENT DOCUMENTS

| | | | | | |
|---|---|---|---|---|---|
| 4,616,814 | A * | 10/1986 | Harwood-Nash et al. | ........ | 5/601 |
| 5,276,927 | A * | 1/1994 | Day | ................. | 5/622 |
| 6,138,302 | A * | 10/2000 | Sashin et al. | ...................... | 5/600 |
| 6,460,206 | B1 * | 10/2002 | Blasche et al. | ................... | 5/601 |
| 6,813,788 | B2 * | 11/2004 | Dinkler et al. | ................... | 5/622 |
| 7,430,773 | B2 * | 10/2008 | Brown et al. | ..................... | 5/601 |
| 7,706,858 | B1 * | 4/2010 | Green et al. | .................. | 600/415 |
| 8,245,335 | B2 * | 8/2012 | Shvartsberg et al. | ............. | 5/601 |
| 2007/0270683 | A1 * | 11/2007 | Meloy | ........................... | 600/415 |
| 2009/0306495 | A1 * | 12/2009 | Scarth et al. | ................ | 600/415 |
| 2010/0249575 | A1 * | 9/2010 | Shvartsberg et al. | ......... | 600/415 |

FOREIGN PATENT DOCUMENTS

| | | |
|---|---|---|
| DE | 9407862 U1 | 9/1995 |
| DE | 102004047509 A1 | 4/2006 |
| DE | 102005029787 A1 | 8/2006 |

OTHER PUBLICATIONS

Noras OP—Kopfhalter für Miyabi, Artikel Nummer: 08115201, Accessory Solutions, http://www.medical.siemens.com/webapp/wcs/stores/servlet/ProductDisplay~q catalo . . . , Siemens AG, 2002-2011.

* cited by examiner

*Primary Examiner* — William Kelleher
*Assistant Examiner* — David R Hare

(57) ABSTRACT

A patient support apparatus is provided. The patient support apparatus has a patient table, a movable support plate for supporting a patient, a guide unit, which is designed to guide the support plate along at least one movement direction of the support plate, and a fastening unit for fastening an auxiliary unit to the support plate. The fastening unit has at least one setting unit for setting the position of the auxiliary unit in relation to the support plate in a flexible manner.

10 Claims, 2 Drawing Sheets

PATIENT SUPPORT APPARATUS AND MEDICAL IMAGING APPARATUS HAVING THE PATIENT SUPPORT APPARATUS

CROSS REFERENCE TO RELATED APPLICATIONS

This application claims priority of German application No. 10 2012 203 119.7 filed Feb. 29, 2012, which is incorporated by reference herein in its entirety.

FIELD OF INVENTION

The present application relates to a patient support apparatus having a patient table, a movable support plate for supporting a patient, a guide unit, which is designed to guide the support plate along at least one movement direction of the support plate, and a fastening unit for fastening an auxiliary unit to the support plate.

BACKGROUND OF INVENTION

Previous patient support apparatuses have a patient table and a support plate for supporting a patient. This support plate is supported in such a manner that it can be moved by a guide unit along a longitudinal extension of the patient support apparatus. The patient support apparatus also has a fastening unit for fastening a head coil unit to the support unit. The head coil unit here is fastened to a contact surface of the support unit.

SUMMARY OF INVENTION

The object underlying the present application is to provide a patient support apparatus, which allows flexible support and/or fastening of an auxiliary unit in different positions in respect of the support unit. The object is achieved by the features of the independent claims. Embodiments are set out in the dependent claims.

The application is based on a patient support apparatus having a patient table, a movable support plate for supporting a patient, a guide unit, which is designed to guide the support plate along at least one movement direction of the support plate, and a fastening unit for fastening an auxiliary unit to the support plate.

It is proposed that the fastening unit has at least one setting unit for setting the position of the auxiliary unit in relation to the support plate in a flexible manner. The auxiliary unit can be disposed in different positions in relation to the support unit. The auxiliary unit is formed by a coil unit, such as a head coil unit, so that the patient, such as the head region of the patient, can be supported in a position desired by an operator and/or in a support position appropriate for the anatomy of the patient. The disclosed patient support apparatus is configured for use in conjunction with a medical imaging apparatus. The integration of the auxiliary unit, such as the head coil unit, on the support plate of the patient support apparatus means that the disclosed patient support apparatus is suitable for a medical imaging apparatus formed by a magnetic resonance apparatus. The movable support plate means that the patient support apparatus can be provided for examinations during or after an intervention by a physician, such as a surgical intervention in a head region of the patient. The patient can remain lying on the support plate and is picked up from an operating table together with the support plate by the patient support apparatus and moved for example to the magnetic resonance apparatus, with the support plate being moved, after the two patient support apparatuses have been docked, from the first patient support apparatus to the second patient support apparatus by the guide unit. As a magnetic resonance examination is frequently used to monitor or continue the surgical intervention, the head of the patient is fixed within the head coil unit during this process, with the head also being able to offer open operating access or open intervention access. The patient support apparatus here is formed by a patient support apparatus for neurosurgical interventions, having an interface for coupling to at least one medical imaging apparatus and having at least one interface for coupling to an operating table, on which the neurosurgical interventions on the patient take place.

It is further proposed that the fastening unit is disposed on a lower face and/or on a front face of the support plate, thereby allowing a space-saving and compact patient support apparatus to be achieved. A "lower face" here refers to a face of the support plate facing away from the support surface. A "front face" here refers to a face disposed in a head support region of the support plate, which is also aligned perpendicular to a longitudinal extension of the support plate.

It is further proposed that the fastening unit has at least one subregion, which extends away from the support plate along a direction from a contact surface toward the lower face, so that the auxiliary unit, such as the head coil unit, can be disposed in an optimum position for the patient and/or the operator, in an appropriate and ergonomic position, as used for example for conventional neurosurgical support of the patient without intraoperative imaging, in relation to the support plate.

The patient support apparatus has a substructure cover, with a region for receiving the fastening unit with a height of 40 mm to 80 mm disposed between the substructure cover and a lower face of the support plate. The region has a height of 50 mm to 70 mm, allowing lowering of the head coil to be achieved during an examination and/or an intervention by a physician. A "region for receiving the fastening unit" here refers to a region between the substructure cover and the lower face of the patient couch, in which no additional units, such as coil elements, cables, etc., are disposed, so that when the support plate is displaced, the fastening unit can move freely within the region for receiving the fastening unit. To this end the region for receiving the fastening unit is of the same height along the entire longitudinal extension of the patient support apparatus.

In one development of the application it is proposed that the support plate is formed by a removable plate, so that the support plate can be used for different support apparatuses, for example in an operating support apparatus, a patient support apparatus for a medical imaging apparatus, etc. The region for receiving the fastening apparatus also allows interference-free movement of the support plate from a first support apparatus to a second support apparatus. A "removable plate" here refers to a support plate for supporting the patient, which can be moved around between different patient support apparatuses. To this end the patient support apparatuses have guide units with slide elements, so that the support plate can be switched without interference and with little friction from a first patient support apparatus to a second patient support apparatus, with the two patient support apparatuses docking with one another for the support plate switch.

It is further proposed that the at least one setting unit has at least one articulation unit for moving and/or setting the position of the auxiliary unit, such as the head coil unit, along at least one spatial direction. This allows the setting of the position of the head coil unit and/or of the head region of the patient to be adjusted in a flexible manner. The setting unit can also have at least one articulation unit for moving and/or setting the position of the auxiliary unit, such as the head coil unit, along at least two spatial directions. Alternatively it is also conceivable for the setting unit also to have a number of articulation units for setting a position and/or movement of the head coil unit. It is thus possible to achieve setting of the position of the auxiliary unit, such as the head coil unit, along a number of spatial directions and thus to adjust the position of the auxiliary unit, such as the head coil unit, to the anatomy of the patient and/or to an optimum treatment position for surgical intervention for example at the head region of the patient. The articulation units here can have a rotary articulation and/or a ball articulation and/or further articulation units that appear expedient to the person skilled in the art. The fastening unit also has a holding region for holding the auxiliary unit, such as the head coil unit.

BRIEF DESCRIPTION OF THE DRAWINGS

Further features and details of the application will emerge from the embodiment described in the following and with reference to the drawings, in which.

DETAILED DESCRIPTION OF INVENTION

Figure 1:
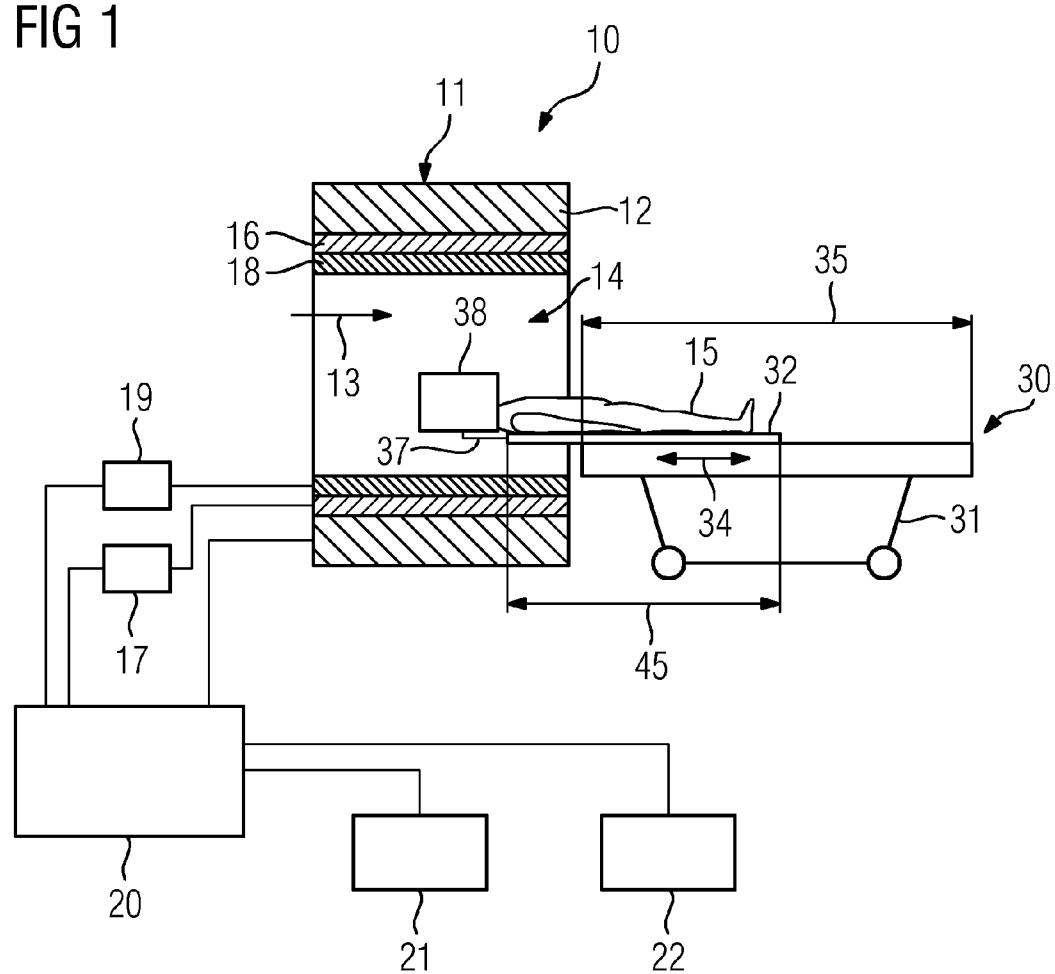
FIG. 1 shows a schematic diagram of a disclosed medical imaging apparatus.

FIG. 1 shows a schematic diagram of a disclosed medical imaging apparatus, formed in the present embodiment by way of example by a magnetic resonance apparatus 10. However the embodiment of the medical imaging apparatus is not restricted to the magnetic resonance apparatus 10; the medical imaging apparatus can of course also be formed by a computed tomography apparatus, a PET apparatus, a mobile or fixed x-ray-based C-arm system, a SPECT apparatus, etc.

The magnetic resonance apparatus 10 comprises a magnetic unit 11 with a main magnet 12 for generating a powerful and constant main magnetic field 13. The magnetic resonance apparatus 10 also has a cylindrical receiving region 14 for receiving a patient 15, the receiving region 14 being enclosed in a peripheral direction by the magnetic unit 11. The patient 15 can be introduced by a patient support apparatus 30 of the magnetic resonance apparatus 10 into the receiving region 14. To this end the patient support apparatus 30 is configured in a movable manner.

The magnetic unit 11 also has a gradient coil 16 for generating magnetic field gradients, which is used for spatial encoding during imaging. The gradient coil 16 is controlled by a gradient control unit 17. The magnetic unit 11 also has a cylindrical high-frequency coil unit 18 and a high-frequency control unit 19 for stimulating polarization, which is established in the main magnetic field 13 generated by the main magnet 12. The high-frequency coil unit 18 is controlled by the high-frequency control unit 19 and emits high-frequency magnetic resonance sequences into an examination space, which is formed by the receiving region 14. This deflects the magnetization from its equilibrium position. Magnetic resonance signals are also received by the high-frequency coil unit 18.

To control the main magnet 12, the gradient control unit 17 and to control the high-frequency control unit 19, the magnetic resonance apparatus 10 has a control unit 20 formed by a computation unit. The computation unit controls the magnetic resonance apparatus 10 centrally, for example the performance of a predefined imaging gradient echo sequence. Control information, such as imaging parameters for example, and reconstructed magnetic resonance images can be displayed to an operator on a display unit 21, for example on at least one monitor, of the magnetic resonance apparatus 10. The magnetic resonance apparatus 10 also has an input unit 22, by which information and/or parameters can be input by an operator during a measuring operation.

The illustrated magnetic resonance apparatus 10 can of course comprise further components that are normally a feature of magnetic resonance apparatuses 10. A general mode of operation of a magnetic resonance apparatus 10 is also known to the person skilled in the art so there is no need for a detailed description of the general components here.

Figure 2:
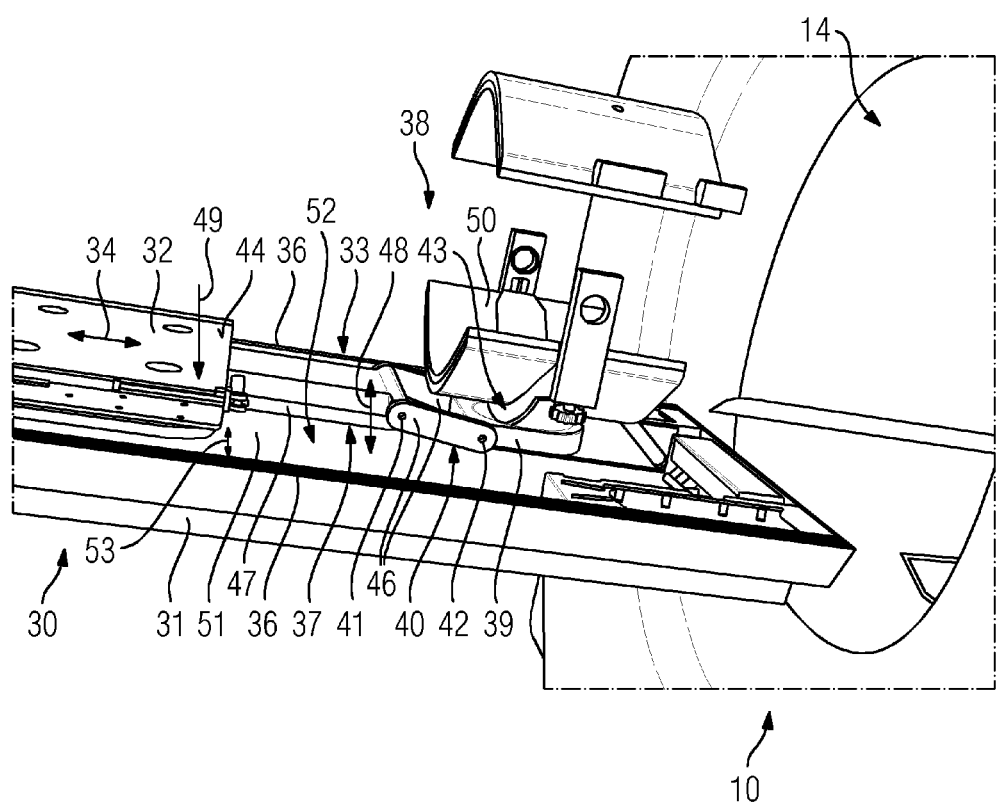
FIG. 2 shows a disclosed patient support apparatus.

The patient support apparatus 30 is shown in more detail in FIG. 2. For use with the magnetic resonance apparatus 10 the patient support apparatus 30 is configured as magnetic resonance-compatible. The patient support apparatus 30 is formed by a patient support apparatus 30 for neurosurgical interventions having an interface for coupling to at least one medical imaging apparatus, such as a magnetic resonance apparatus 10, and having at least one interface for coupling to an operating table (not shown in detail).

The patient support apparatus 30 has a table 31 and a movable support plate 32 for supporting the patient 15. The patient support apparatus 30 also has a guide unit 33, which is designed to guide the support plate 32 along a movement direction 34 of the support plate 32. The movement direction 34 here is aligned parallel to a longitudinal extension 35 of the patient support apparatus 30.

The guide unit 33 has two guide rails 36, each disposed on a side peripheral region of the table 31 along the longitudinal extension 35 of the patient support apparatus 30. The guide rails 36 here are provided with slide elements (not shown in detail), which can be formed by roller slide elements and/or other slide elements that appear expedient to the person skilled in the art. This allows the support plate 32 to be moved and/or guided with little friction along the longitudinal extension 35 in relation to the table 31. The support plate 32 can also have slide elements and/or guide elements (not shown in detail), such as for example guide rails, of the guide unit 33. The guide unit 33 supports the support plate 32 in such a manner that it can be moved along the longitudinal extension 35, it being possible to switch from the patient support apparatus 30 to an operating table support apparatus in the process. To this end the support plate 32 is formed by a removable plate.

The patient support apparatus 30 also has a fastening unit 37 for fastening an auxiliary unit formed by a head coil unit 38. In one alternative embodiment of the application the auxiliary unit can also be formed by further units or elements.

The fastening unit 37 has a holder 39, within which the head coil unit 39 is disposed. The fastening unit 37 is configured in such a manner that it is possible to set the position of the head coil unit 38 in relation to the support plate 32 in a flexible manner. To this end the fastening unit 37 has a setting unit 40, which comprises at least one articulation unit 41, 42, 43. In the present embodiment the setting unit 40 has three articulation units 41, 42, 43. The first articulation unit 41 is formed by a first rotary articulation unit and the second articulation unit 42 is formed by a second rotary articulation unit. The first rotary articulation unit and the second rotary articulation unit are disposed parallel to one another, with a rotation axis of the first rotary articulation unit and a rotation axis of the second rotary articulation unit disposed parallel to one another. The two rotation axes are also disposed parallel to a contact surface 44 of the support plate 32 and orthogonal to a longitudinal extension 45 of the support plate 32. The two rotary articulation units are connected to one another by way of two bars 46 disposed parallel to one another.

The first rotary articulation unit allows a rotational movement of the two parallel bars 46 about the rotation axis of the first rotary articulation unit in relation to a holding element 47 of the fastening unit 37 connected in a fixed manner to the support plate. The second rotary articulation unit allows a rotational movement of the two parallel bars 46 about the rotation axis of the second rotary articulation unit in relation to the holder 39 for arranging the head coil unit 38. When the position of the head coil unit 38 is being set, the two rotary articulation units allow said head coil unit 38 to be displaced along the longitudinal extension 45 of the support plate 32 and along a second spatial direction 48, which is aligned perpendicular to the longitudinal extension 45 of the support plate 32 and perpendicular to the support surface 44 of the support plate 32.

The holder 39 for arranging the head coil unit 38 also has the third articulation unit 43 of the setting unit 40, which comprises a rotary articulation unit. A rotation axis of said third rotary articulation unit is aligned perpendicular to the rotation axes of the first and second rotary articulation units and also perpendicular to the support surface 44 of the support plate 32. This allows a rotation of the head coil unit 38 parallel to the support surface 44 of the support plate 32 to be achieved. The third articulation unit 43 can also produce a rotation of the head coil unit 38 within the plane aligned perpendicular to the contact surface 44 of the support plate 32.

Alternatively or additionally the setting unit 40 and/or the individual articulation units 41, 42, 43 of the setting unit 40 can also be embodied differently from a rotary articulation unit. For example the articulation units 41, 42, 43 can also be formed by ball articulation units, rotary push-in articulation units and/or further articulation units that appear expedient to the person skilled in the art. It is also conceivable for the number of articulation units to vary, when individual articulation units can be set with a number of degrees of freedom.

The setting of the fastening unit 37, such as of the setting unit 40, for a desired position of the head coil unit 38 is effected manually here by an operator, for example a clinician. Alternatively or additionally at least partially automatic and/or self-activated setting of the position of the head coil unit 38 by the setting unit 40 is conceivable, for example by an electric or electronic setting unit, etc.

The fastening unit 37 is disposed on the support plate 32 of the patient support apparatus 30. To this end the fastening unit 37 is disposed in a fixed manner with the holding element 47 on the support plate 32, the arrangement being effected on a lower face formed by a face of the support plate 32 facing away from the support surface 44 and/or on a front face of the support plate 32. In the present embodiment the fastening unit 37 is disposed on the lower face of the support plate 32. The holding element 47 of the fastening unit 37 here can be screwed, bonded or riveted to the support plate 32 and/or can be connected in a fixed manner to the support plate 32 by further fastening methods.

The arrangement of the fastening unit 37 on the lower face and/or on the front face of the support plate 32 means that the fastening unit 37 projects beyond the dimensions of the support plate 32. The fastening unit 37 projects beyond the support plate 32 along a direction 49 from the support surface 44 toward the lower face of the support plate 32. Depending on the position set at the fastening unit 37, the fastening unit 37 can have a maximum extension of approx. 70 mm relative to the support plate 32 along this direction 49. The maximum extension has a length of approx. 60 mm and a length of approx. 50 mm. The fastening unit 32 also projects beyond the front face along the longitudinal extension 45 of the support plate 32, so that, when mounted on the fastening unit 37, the head coil unit 38 is disposed outside the dimensions of the support plate 32 along the longitudinal extension 45 of the support plate 32. It is possible for the head coil unit 38, a bearing surface 50 of the head coil unit 38 for contact with the head of a patient 15, to be lowered to and/or disposed at the height of the contact surface 44 by the fastening unit 37, such as by the setting unit 40.

The patient support apparatus 30, such as the table 31, also has a substructure cover 51, which is designed to cover a region for receiving a controller, an electronic unit and/or further units and/or elements that appear expedient to the person skilled in the art, and which covers a face of the patient table 31 facing the support plate 32. For interference-free movement of the support plate 32 together with the lowered head coil unit 38 relative to the substructure cover 51, the patient support apparatus has a region 52 for receiving the fastening unit 37, with the fastening unit 37 projecting out from the support plate 32 into said region 52. This region 52 for receiving the fastening unit 37 has a height 53 of approx. 40 mm to approx. 80 mm, however a height 53 of 50 mm to 70 mm and a height 53 of at least 55 mm. This region 52 for receiving the fastening unit 37 has the same height 53 along the entire longitudinal extension 35 of the patient support apparatus 30. Said region 52 also extends along an entire transverse extension between the two guide rails 36 of the table 31, so that unwanted tilting of the fastening apparatus 37 is prevented during movement of the support plate 32 along the longitudinal extension 35.

The invention claimed is:

1. A patient support apparatus, comprising:
   a patient table;
   a support plate for supporting a patient;
   a guide unit for guiding the support plate along at least one movement direction of the support plate;
   an auxiliary unit;
   a fastening unit for fastening the auxiliary unit to the support plate;
   a setting unit for flexibly setting a position of the auxiliary unit in relation to the support plate; and
   a substructure cover that covers a region for receiving the fastening unit and covers a face of the patient table facing the support plate, wherein the region has a height of 40 mm to 80 mm and is disposed between the substructure cover and a lower face of the support plate,
   where the fastening unit comprises a holder for disposing the auxiliary unit and a holding element connected to the support plate,
   wherein the setting unit comprises a first articulation unit and a second articulation unit,
   wherein the first articulation unit and the second articulation unit are connected to one another by two bars, and
   wherein the first articulation unit rotates the two bars in relation to the holding element and the second articulation unit rotates the two bars in relation to the holder for flexibly setting the position of the auxiliary unit in relation to the support plate along a longitudinal extension of the support plate and along a second spatial direction that is perpendicular to the longitudinal extension of the support plate.

2. The patient support apparatus as claimed in claim 1, wherein the auxiliary unit is formed by a head coil unit.

3. The patient support apparatus as claimed in claim 1, wherein the fastening unit is disposed on a lower face and/or on a front face of the support plate.

4. The patient support apparatus as claimed in claim 3, wherein the fastening unit comprises at least one subregion that extends away from the support plate along a direction from a contact surface toward the lower face.

5. The patient support apparatus as claimed in claim 1, wherein the region has a height of 50 mm to 70 mm.

6. The patient support apparatus as claimed in claim 1, wherein the region has a same height along entire longitudinal extension of the patient support apparatus.

7. The patient support apparatus as claimed in claim 1, wherein the support plate is formed by a removable plate.

8. A medical imaging apparatus, comprises:
a patient support apparatus as claimed in claim 1.

9. The medical imaging apparatus as claimed in claim 8, wherein the medical imaging apparatus is a magnetic resonance apparatus.

10. The patient support apparatus as claimed in claim 1, wherein the setting unit comprises a third articulation unit that rotates the auxiliary unit parallel to a support surface of the support plate.

* * * * *